United States Patent [19]

Childs

[11] 4,059,633
[45] Nov. 22, 1977

[54] RECOVERY OF HEXAFLUOROACETONE FROM A HEXAFLUOROACETONE-HF CONTROL

[75] Inventor: William V. Childs, Bartlesville, Okla.

[73] Assignee: Phillips Petroleum Company, Bartlesville, Okla.

[21] Appl. No.: 605,124

[22] Filed: Aug. 15, 1975

[51] Int. Cl.² .............................................. C07C 49/16
[52] U.S. Cl. ............................ 260/593 H; 260/593 P
[58] Field of Search ................ 260/593, 593 H, 593 P

[56] References Cited

U.S. PATENT DOCUMENTS

| 3,185,734 | 5/1965 | Fawett et al. | 260/593 H |
| 3,382,222 | 5/1968 | Pittman et al. | 260/593 H |
| 3,433,838 | 3/1969 | Cunningham et al. | 260/593 H |
| 3,544,633 | 1/1967 | Yodis et al. | 260/593 H |
| 3,745,093 | 7/1973 | Lee | 260/593 H |

*Primary Examiner*—James O. Thomas, Jr.
*Assistant Examiner*—James H. Reamer

[57] ABSTRACT

A process for recovery of hexafluoroacetone from the hexafluoroacetone-HF complex by contacting the complex with acetic anhydride under reaction conditions. The reaction produces liberated hexafluoroacetone and by-products, acetyl fluoride and acetic acid. The by-products can be further reacted in a cyclic process whereby acetic anhydride is regenerated for recycle.

8 Claims, 1 Drawing Figure

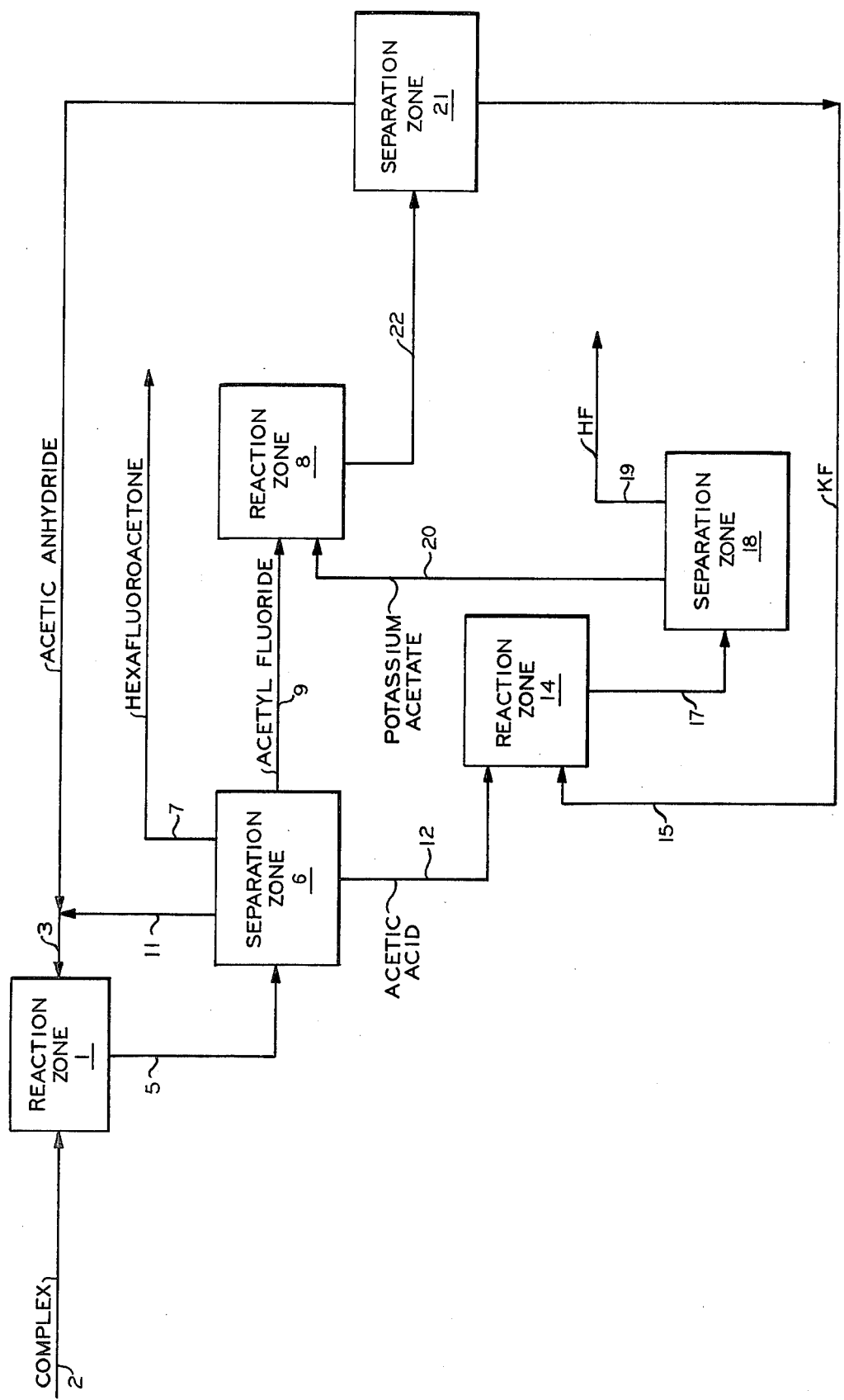

RECOVERY OF HEXAFLUOROACETONE FROM A HEXAFLUOROACETONE-HF CONTROL

The present invention relates to a process for the recovery of hexafluoroacetone from a complex of hexafluoroacetone-HF. Both chemical and electrochemical processes are known by which hexafluoroacetone can be produced. Generally, however, hydrofluoric acid (HF) is the reagent in these processes and when it is, a hexafluoroacetone-HF complex is formed to some degree. This complex is particularly stable and it is difficult to separate and recover the hexafluoroacetone from the complex. A number of procedures to effect the separation have been devised, one of which employs the use of liquified sulfur trioxide, for example. The present invention provides an alternative process for recovering the hexafluoroacetone from the hexafluoroacetone-HF complex.

The principal object of the present invention is to provide a process for recovering hexafluoroacetone from a hexafluoroacetone-HF complex and to provide such a process wherein certain reaction products can be further reacted so that the total process can be made a cyclic type of process.

Other objects and advantages of the present invention will become apparent from the following detailed description wherein are set forth by way of illustration and example certain embodiments of the present invention.

FIG. 1 is a diagrammatic illustration of the process for recovering hexafluoroacetone from a hexafluoroacetone-HF complex.

As required, detailed embodiments of the present invention are disclosed herein, however, it is to be understood that the disclosed embodiments are merely exemplary of the invention which may be embodied in various forms. Therefore, specific details disclosed herein are not to be interpreted as limiting but merely as a basis for the claims and as a representative basis for teaching one skilled in the art to variously employ the present invention in virtually any appropriate manner.

Hexafluoroacetone can be produced in any suitable manner such as by a chemical process or an electrochemical process wherein hydrofluoric acid is a reagent and in the process of producing hexafluoroacetone, a complex of hexafluoroacetone-HF is formed. The HF-containing complex can be contacted under reaction conditions with acetic anhydride to form liberated hexafluoroacetone and by-products, acetic acid and acetyl fluoride. Preferably, the reaction by-products, acetic acid and acetyl fluoride, can be further reacted to form acetic anhydride which can be recycled and hydrogen fluoride which can be used, e.g., in electrochemical fluorination.

Generally, the steps of the cyclic process include reacting the hexafluoroacetone-HF complex with acetic anhydride to liberate hexafluoroacetone in separable form and to produce acetyl fluoride and acetic acid as by-products. The products of the first reaction are separated as hexafluoroacetone, acetyl fluoride and acetic acid. The separated acetyl fluoride can then be reacted with an alkali metal or alkaline earth metal acetate (hereinafter referred to as a metal acetate) such as potassium acetate, to regenerate acetic anhydride for use in the first reaction. The second reaction also produces an alkali metal or alkaline earth metal fluoride (hereinafter referred to as a metal fluoride) such as preferably potassium fluoride which is then used in a third reaction. The third reaction includes the reaction of the acetic acid with the metal fluoride which will then liberate recoverable HF and produce metal acetate which can be recycled for use in the second reaction.

The above reactions are shown by exemplary reaction equations listed below:

Reaction (1): Treatment of the hexafluoroacetone-hydrogen fluoride complex (A) with acetic anhydride (B) to liberate hexafluoroacetone (A') and by-products acetic acid (C) and acetyl fluoride (D)

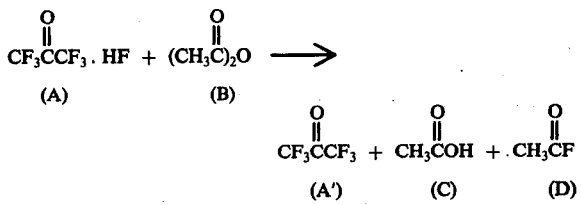

Reaction (2): Treatment of acetyl fluoride (D) from reaction (1) with potassium acetate (E) from reaction (3) to give acetic anhydride (B) for recycle to reaction (1), and potassium fluoride (F)

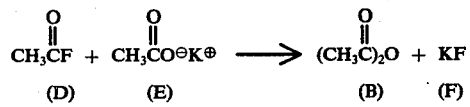

Reaction (3): Treatment of acetic acid (C) from reaction (1) with potassium fluoride (F) from reaction (2) to give potassium acetate (E) for use in reaction (2) and recovered fluorine value equivalents in the form of hydrogen fluoride (G)

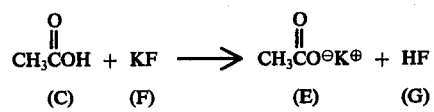

The above process can be carried out regardless of the manner in which the complex is produced, e.g., whether it is produced by an electrochemical fluorination of acetone, fluorination of hexachloroacetone or any other suitable chemical reaction.

Although the hexafluoroacetone-HF complex is believed to consist of about equimolar quantities of these two materials, the complexes are frequently associated with additional quantities of HF. Thus, in the difficulty separable compositions containing the complex which are suitable as a feedstock for the present invention, the molar ratio of HF to hexafluoroacetone can range from about 1:1 to 3:1 but more generally from about 1:1 to about 2:1.

In reaction (1) of the above described process, the hexafluoroacetone-HF complex and acetic anhydride can be reacted either batchwise or continuously under suitable conditions of temperature, pressure and contact time to give the desired hexafluoroacetone product along with the by-products, acetic acid and acetyl fluoride. Generally, the hexafluoroacetone-HF complex and acetic anhydride are used in approximately 1:1 molar ratio of anhydride to HF, although ratios of up to 2:1 can be used. The excess acetic anhydride can be recovered for recycle in a suitable manner such as by distillation. The reaction of the acetic anhydride and hexafluoroacetone-HF complex is normally carried out in the temperature range of −10° C to +100° C in the absence of a diluent and in the pressure range of 10 psig to 500 psig. The reaction is an equilibration and the reactants and products are maintained essentially in a liquid state. The approximate normal boiling points of the reactants and products are as follows: hexafluoroacetone-HF complex 11°–12° C, acetic anhydride 140° C, hexafluoroacetone −29° C, acetyl fluoride 21° C, and acetic acid 117° C. The residence time for the equilibration of the acetic anhydride and hexafluoroacetone-HF complex varies over the range of approximately 0.1 to 100 minutes but preferably within the range of 1.0 to 10 minutes. To prevent equipment damage and contamination of the process, the apparatus used to conduct the reaction is preferably of a stainless steel such as 316 or a corrosion resistant alloy such as Inconel.

The equilibration of the hexafluoroacetone-HF complex with acetic anhydride strongly favors the production of hexafluoroacetone, acetyl fluoride and acetic acid and this mixture of products can be readily separated such as by fractionation in a conventional stainless steel column to give an overhead product of hexafluoroacetone and a bottom mixture of acetic acid and acetyl fluoride. The bottoms mixture, which can contain any excess of acetic anhydride from the equilibration zone, can be fractionated or otherwise separated to give an overhead product of acetyl fluoride which can be used for reaction with the metal acetate as described above, which is preferably potassium acetate, to prepare additional acetic anhydride and potassium fluoride. Also produced in this separation process is a kettle residue of acetic acid which can contain any excess of acetic anhydride. If acetic anhydride is present, same can be separated such as by fractionation to recover overhead acetic acid which can be reacted with the potassium fluoride to give potassium acetate and recovered fluorine equivalents in the form of HF. The kettle bottoms after the separation will be acetic anhydride which can be recycled to equilibrate with the hexafluoroacetone-HF complex.

The reaction of the by-product acetyl fluoride with metal acetate such as potassium acetate is carried out under suitable reaction conditions of time, temperature and pressure which are sufficient to produce a metal fluoride such as potassium fluoride and acetic anhydride. Preferably, a pressure is maintained which is sufficient to maintain the acetyl fluoride essentially in the liquid phase at a temperature in a broad range of 20° to 200° C and more preferably in a temperature range of 80° to 150° C. The time required for the reaction is approximately 10 minutes to 24 hours and, more preferably, in a range of 1 to 8 hours. The produced potassium acetate and acetic anhydride are suitably separated such as by flash distilling, recovering the acetic anhydride as an overhead product which can be recycled for equilibration with additional hexafluoroacetone-HF complex. The remaining potassium fluoride which is produced in this reaction is transferred to a suitable reactor for contacting with acetic acid.

The reaction of acetic acid and metal fluoride such as potassium fluoride is carried out under suitable reaction conditions of time, temperature and pressure which are sufficient to produce HF and a metal acetate such as potassium acetate. Thus, acetic acid recovered by fractionation as described above can be contacted at elevated temperature such as the reflux temperature with potassium fluoride for a time of approximately 10 minutes to 24 hours and, more preferably, 1 hour to 8 hours so as to yield HF and potassium acetate. The HF can be recovered in any suitable manner such as by fractionation at approximately 50 psig which pressure conveniently allows condensation of the HF with cooling tower water of approximately 100° F. The unreacted acetic acid can then be flash distilled and recovered for reuse and the residual potassium acetate is transferred for reaction with the acetyl fluoride as described above.

Referring more in detail to FIG. 1, the above-described process can be more fully described. Hexafluoroacetone-HF complex and acetic anhydride are introduced into a reaction zone 1 through conduits 2 and 3, respectively. The equilibrated mixture of reactants along with the products acetyl fluoride, hexafluoroacetone and acetic acid are passed through a conduit 5 to a separation zone 6 to separate the desired hexafluoroacetone from the by-products acetyl fluoride and acetic acid. The hexafluoroacetone is recovered through a conduit 7. Acetyl fluoride is passed to a reactor 8 via conduit 9. Unreacted acetic anhydride from the separation zone 6 can be recycled to the reaction zone 1 by means of a conduit 11. The acetic acid from the separation zone 6 is passed through a conduit 12 to another reaction zone 14. In this reaction zone 14, the acetic acid and potassium fluoride introduced via conduit 15 are contacted to give hydrogen fluoride and potassium acetate. The reaction mixture from the reactor 14 is conducted via a conduit 17 to another separation zone 18 from which HF is recovered via a conduit 19. The potassium acetate passes to the reaction zone 8 via a line 20.

In the reaction zone 8 acetyl fluoride from the separation zone 6 is contacted with potassium acetate from the separation zone 18. The reaction mixture from the reaction zone 8 is conducted to a separation zone 21 via a line 22. The recovered acetic anhydride is passed from the separation zone 21 to the reaction zone 1 via the line 3 whereas the recovered potassium fluoride is transferred to the reaction zone 14 via the conduit 15.

Certain equipment such as valves, pumps, heat exchangers, solids conveyors, etc. which are well known to those skilled in the art, have been omitted from this drawing as same is only presented to illustrate diagrammatically the above-described process. The reaction zones and separation zones are of a construction which are well known to those skilled in the art and need not be described herein.

The separation zones of the Figure can comprise one or more conventional separation units such as fractionators, filters, evaporators, etc., as is appropriate. In some instances, particularly when a given chemical step is operated batchwise, the separation zone can be a part of the reaction zone. For example, a reaction vessel, after the reaction is complete, can become the distillation kettle for the subsequent fractional distillation step.

By way of illustrating the present invention, the following specific example is provided.

EXAMPLE

A difficultly separable hexafluoroacetone-HF complex mixture containing about 1.01 g-moles hexafluoroacetone and 1.54 g-moles HF was contacted with 2.22 g-moles acetic anhydride at 100 psig. The temperature of the mixture rose from 20° to 31° C within a few minutes. A 411.0 g portion of this mixture was then fractionated at atmospheric pressure using a Freon 11/dry ice cooling bath and a 27½ inch × 7/16 inch column packed with Helipak Monel. A 135.7 g hexafluoroacetone fraction, an 80.4 g intermediate fraction, and an 85.0 g acetic fluoride fraction were obtained leaving a 147.5 g kettle product of acetic hydride and acetic acid. A gas-liquid chromatographic analysis of the samples showed that the purity of the hexafluoroacetone fraction was 90 area percent. However, to demonstrate that a higher purity hexafluoracetone could be obtained, a portion of the overhead and kettle products were recombined, the mixture was redistilled, and a hexafluoroacetone fraction having a purity of 99.9 area percent was obtained.

It is to be understood that while I have described certain forms of my invention, it is not to be limited to the specific form of the present invention disclosed herein.

What I claim and desire to secure by Letters Patent is:

1. A process of removing hexafluoroacetone from a hexafluoroacetone-HF complex, represented by the formula $$CF_3\overset{O}{\overset{\|}{C}}CF_3 \cdot HF$$

comprising the steps of:
   a. contacting said hexafluoroacetone-HF complex with acetic anhydride under suitable reaction conditions to produce a first reaction effluent comprising hexafluoroacetone, acetyl fluoride and acetic acid; and
   b. separating hexafluoroacetone from said first reaction effluent.

2. A process as set forth in claim 1 including:
   a. separating thus produced acetyl fluoride from said first reaction effluent;
   b. reacting thus separated acetyl fluoride with one of an alkali metal acetate and an alkaline earth metal acetate to produce a second reaction effluent comprising acetic anhydride and the corresponding one of an alkali metal fluoride and alkaline earth metal fluoride; and
   c. separating thus produced acetic anhydride from thus produced alkali metal fluoride or alkaline earth metal fluoride.

3. A process as set forth in claim 2 including:
   a. recycling thus separated acetic anhydride to the step of contacting acetic anhydride with hexafluoroacetone-HF complex.

4. A process as set forth in claim 2 including:
   a. separating thus produced acetic acid from said first reaction effluent;
   b. reacting thus separated acetic acid with thus produced alkali metal fluoride or alkaline earth metal fluoride to produce HF and the corresponding alkali metal acetate or alkaline earth metal acetate; and
   c. separating thus produced alkali metal acetate or alkaline earth metal acetate from thus produced HF.

5. A process as set forth in claim 4 including:
   a. recycling thus separated alkali metal acetate or alkaline earth metal acetate for reaction with thus separated acetyl fluoride.

6. A process for removing HF from a hexafluoroacetone-HF complex, represented by the formula $$CF_3\overset{O}{\overset{\|}{C}}CF_3 \cdot HF$$

comprising the steps of:
   a. contacting a hexafluoroacetone-HF complex with acetic anhydride under suitable reaction conditions to produce a first reaction effluent comprising hexafluoroacetone, acetyl fluoride and acetic acid;
   b. separating the first reaction effluent into a hexafluoroacetone portion, an acetyl fluoride portion and an acetic acid portion;
   c. reacting the thus separated acetyl fluoride portion with one of an alkali metal acetate and an alkaline earth metal acetate to produce a second reaction effluent comprising acetic anhydride and the corresponding one of an alkali metal fluoride and alkaline earth metal fluoride;
   d. separating the second reaction effluent into an acetic anhydride portion and a portion comprising alkali metal fluoride or alkaline earth metal fluoride;
   e. recycling thus separated acetic anhydride portion to the step of contacting acetic anhydride with hexafluoroacetone-HF complex;
   f. reacting thus separated acetic acid with thus separated alkali metal fluoride or alkaline earth metal fluoride to produce an alkali metal acetate or alkaline earth metal acetate and HF;
   g. separating thus produced alkali metal acetate or alkaline earth metal acetate and HF; and
   h. recycling thus separated alkali metal acetate or alkaline earth metal acetate for reaction with thus separated acetyl fluoride.

7. A process as set forth in claim 1 wherein:
   a. the hexafluoroacetone-HF complex and acetic anhydride are contacted under reaction conditions of between approximately $-10°$ and $100°$ C and 10 psig and 500 pisg.

8. A process as set forth in claim 2 wherein:
   a. the thus separated acetyl fluoride and the alkali metal acetate or alkaline earth metal acetate are reacted at between about $20°$ C and $200°$ C.

* * * * *